(12) United States Patent
Cid Vivanco et al.

(10) Patent No.: US 8,334,001 B2
(45) Date of Patent: Dec. 18, 2012

(54) COMPOSITION COMPRISING MUCILAGINOUS POLYSACCHARIDES DERIVED FROM ALOE BARBADENSIS AND METHOD FOR OBTAINING SAME AND USE THEREOF

(75) Inventors: Roberto Cid Vivanco, Quito (EC); Renato Andrade Bejarano, Quito (EC); Diego Patricio Sandoval Torres, Quito (EC)

(73) Assignee: Pharmabrand S.A., Quito (EC)

(*) Notice: Subject to any disclaimer, the term of this patent is extended or adjusted under 35 U.S.C. 154(b) by 191 days.

(21) Appl. No.: 12/733,738

(22) PCT Filed: Jun. 6, 2008

(86) PCT No.: PCT/EC2008/000006
§ 371 (c)(1),
(2), (4) Date: Jun. 9, 2010

(87) PCT Pub. No.: WO2009/036771
PCT Pub. Date: Mar. 26, 2009

(65) Prior Publication Data
US 2010/0285110 A1     Nov. 11, 2010

(30) Foreign Application Priority Data
Sep. 21, 2007 (EC) ........................................ 07-7764

(51) Int. Cl.
*A01N 65/00* (2009.01)
(52) U.S. Cl. ........................................................ 424/725
(58) Field of Classification Search .................. None
See application file for complete search history.

(56) References Cited

U.S. PATENT DOCUMENTS

| 6,007,796 A | 12/1999 | Menzel et al. |
| 6,146,650 A | 11/2000 | Redlinger |
| 2003/0095959 A1 | 5/2003 | Mayne |
| 2004/0057917 A1 | 3/2004 | Wolf et al. |
| 2004/0170676 A1 | 9/2004 | Jordan |
| 2005/0191267 A1 | 9/2005 | Luanratana |

FOREIGN PATENT DOCUMENTS

| ES | 2154896 T3 | 4/2001 |
| WO | 99/13717 A1 | 3/1999 |
| WO | 00/66071 A1 | 11/2000 |
| WO | 2006/084353 A1 | 8/2006 |

*Primary Examiner* — Michael Meller
(74) *Attorney, Agent, or Firm* — Nath, Goldberg & Meyer; Tanya E. Harkins

(57) ABSTRACT

Provided is a composition including mucilaginous polysaccharides of *aloe barbadensis*, including for example aloeride and acemannan, and phospholipids, including for example, sphingosomes, ceramides and liposomes in combination with collagen, for the treatment of premature aging, overexposure to ultraviolet rays, and acne. Also provided is a process for preparing the composition.

7 Claims, No Drawings

COMPOSITION COMPRISING MUCILAGINOUS POLYSACCHARIDES DERIVED FROM ALOE BARBADENSIS AND METHOD FOR OBTAINING SAME AND USE THEREOF

This is a National Phase Application filed under 35 U.S.C. 371 as a national stage of PCT/EC2008/000006, with the filing date of Jun. 5, 2008 an application claiming the benefit to Ecuadorian Application No. SP 07-7764, filed on Sep. 21, 2007, the entire content of each of which is hereby incorporated by reference in its entirety.

TECHNICAL FIELD

The invention refers to new compositions where the metabolites of the *aloe barbadensis*, particularly aloeride and acemannan, have an antiseptic, hydrating, keratolitic and photoprotective activity. Its activity is broadened by synergy action of the phospholipids; particularly the liposomes in combination with collagen.

BACKGROUND OF THE INVENTION

Background of *Aloe Barbadensis*—

The *Aloe barbadensis* is a tropical or subtropical plant of the Liliacea family, whose leaves grow in the form of a rosette around the center stem. These leaves are formed by a viscous and moderately translucent gel that determines the structural rigidity of the plant, which has been used for centuries by those who live where it grows naturally, and has been used as a health and beauty aid.

The *aloe barbadensis* has been traditionally used to treat digestive disorders, such as irritable bowel syndrome, ulcerative colitis, Crohn's disease, peptic ulcers; also as a nutritional supplement, detoxing tonic, and more often in beauty treatments, as it aids in the absorption of moisture by the skin. Depending on the quality of the gel, it is used to decrease the pain due to sunburns. If exposed to the environment for long periods of time, it will lose its therapeutic power.

The *aloe vera barbadensis* whose active principles are the ones that structure the compound, are found in the adult base leafs of the plant; the gel obtained is translucent, viscous, mucilaginous, contains several polysaccharides, considered responsible for the beneficial properties.

The metabolites as the aloeride and acemannan, are related to the immunologic and anti-inflammatory properties of this plant.

The aloeride, a polysaccharide, increases the TNF-alfa, likewise the acemannan is a carbohydrate used in a concentration of 200 µg/ml, produces an activation of the necrosis factor, kappa B, the effect is shown in concentrations of only 0.015% of the aloeride.

Background of Liposomes—

Liposomes act as transporters and are vesicles that possess a lipid bi-layer. Taking advantage of the bio affinity of liposomes, they are used with the purpose of incorporating various drugs into the body.

Additives may be used with this art, which interact with the liposomes and that may include: antiseptics, antihistamines, (difenhidramine, clorofeniramine maleate), vitamins (A and its esters, B-complex, E and its esters) topical anesthetics (lidocaine, procaine), refreshers (1-menthol, borneol, mentha oil), polymer additives (polietilenglicol, hydroxyethyl cellulose, isotonic agents (sodium chloride).

Liposomes may be applied in the form of a watery suspension or in the form of a composition of a physiologically accepted vehicle, where the liposome has been incorporated. The vehicle may be a cleansing cream, a gel for skin application, a lotion or ointment. Temperature conditions should be managed when they are incorporated.

Problem of the State of the Art—

A healthy, elastic and well-hydrated skin is constituted by a morphologically integral epidermis, for it to meet all physiological requirements of its nature. With the loss of water due to multiple factors, the skin becomes dry, rough and prone to being victim of pathogens. Emollient substances, fats, phospholipids and sterols return the flexibility and elasticity to the skin, for short periods of time.

The common condition of dry skin is attributable to various factors, which include: relative external atmospheric humidity, disorganization of lipid membranes, disruption of the lipid membranes plus loss of water for hygroscopic substances.

When relative external humidity is low, a rapid loss of water from the skin to the external environment is produced; the loss of water from the skin is faster than the capability of replacement by migration from the dermal tissues.

The application of moisturizers temporarily improves skin dryness, water vapor migrates to these areas, but it is not retained and it is lost in the atmosphere.

The problem previously mentioned has not been resolved completely as the existing creams only offer a protective film with conventional hydrants, allowing the temporary slowing down of loss of water.

On the other hand, the skin of a mammal, especially a human, is not only an organ for external protection, it has a multifunctional activity, specialized in some activities such as: sweating, transpiration, sensory information and production of oil.

An important activity related to the protection of skin integrity is the sebum, which is secreted by the sebaceous glands, located in the base of the pilous follicle. It allows lubrication, being able to generate a humid microenvironment that favors self-protection from the external environment.

During puberty with the numerous physiological changes that in some cases are produced by the increase in testosterone levels, the sebaceous glands increase in size and secrete more sebum than usual. There is also production of keratin; main constituent of the pilous follicle and of the skin, where excess keratin and sebum clog skin pores forming a spot or blackhead.

In some circumstances there is inflammation of this area resulting in zits and/or pimples; condition known as acne vulgaris. This phenomenon appears in areas where there are a great number of sebaceous glands: face, neck, back, and shoulders. If the presence of the anaerobic bacteria Propionibacterium acnes is added, there will be infectious acne, resulting in what is known as cystic acne, a more severe form of the disease.

In nodular acne, the mix of sebum within the gland with necrotic cells, plus a rupture in the follicle wall, causes a cyst in the skin.

The Propionibacterium acnes is a gram-negative anaerobic bacteria, it releases lipases to digest the sebum produced by the sebaceous gland and is liberated into the pore. The combination of enzymes and the products of the digestion stimulate and generate an intense local inflammation of the cells, affecting the pore, and also affecting the pilous follicle especially when it opens, creating what is known as a spot or blackhead.

In the waterfall of events in the skin an inflammatory event develops on the surface of the same, which results in the formation of a pimple.

The majority of processes for acne mitigation center on acting over the sebum, through agents such as alcohol, hydrogen peroxide, salicylic acid, benzoyl peroxide, antibiotics applied topically or taken orally, such as eritromicine, tetracycline, generally employed for bacterial control.

Vitamins and herbs are also often used to treat acne, frequently employing vitamin A but with the corresponding side effects. Popular treatments involve the use of isotretinoin, (retinoic acid in its acid form) combined or not with chemical products.

Additionally some preparations contain herbs such as azafras.

All these treatments generally lead to side effects such as dryness of the skin.

BACKGROUND OF PATENT APPLICATIONS

There have been previous patent applications related to compositions where one of the ingredients is *Aloe barbadensis* extract, as well as patent applications for compositions related to liposomes, but in the state of the art there are no patent applications that contemplate in one sole composition the *Aloe barbadensis* extract and liposomes to obtain the desired synergy effect. The mentioned patent applications include the following:

MXPA06004123, date of publication: Jul. 5, 2006. This Mexican patent application deals with a topic cosmetic composition to provide human skin that looks notably healthy. The composition comprises a topical cosmetic carrying vehicle that includes vitamin A, vitamin E, *aloe* and other components.

MXP0009966, date of publication: Dec. 11, 2001. This Mexican patent application provides a method for isolating mucilaginous polysaccharides from plants, cereals, cell cultures or fungi that have mucilaginous polysaccharides or that are linked to a protein with desired biological properties.

CLP199701392, date of publication: Apr. 27, 1998. This patent application provides a fluid gel for skin care, having an antiseptic action, keratolytic action, and that provides a soft, refreshing sensation when applied to the skin. Said gel contains a rejuvenating agent, a hydrating agent, sodium PCA, a skin-repairing agent, *aloe* extract, amongst other components.

Likewise, the patent applications and granted patents RU 2 299 725, RU 2184527, U.S. Pat. No. 6,238,652, U.S. Pat. No. 4,302,443, amongst others, refer to compositions that contain *aloe vera*.

KR900008312, date of publication: Nov. 12, 1990. Refers to cosmetic compositions containing mixtures of liposomes using nonionic active agents.

The patent applications WO 2006/098699, U.S. Pat. No. 6,080,425, SK 143493, EP 0 450 352, FR 2668485 and FR 2 668 485 make reference to creams or gels containing liposomes in their composition.

DESCRIPTION OF THE INVENTION

It seeks to develop a preparation that avoids future acne events and that does not generate side effects, furthermore; that it also maintains good hydration, concomitantly protects the epithelial tissue from adverse environmental conditions, thus providing photoprotection and avoiding premature aging of the same.

All the problems mentioned in previous paragraphs have been solved with the new compositions of the present invention, compositions constituted by *Aloe barbadensis* metabolites with phospholipids, particularly liposomes. This combination achieves a potent synergy effect.

In addition to developing a procedure for obtaining these new compositions, said process is developed under specific conditions in accordance to the requirements.

In the previous cases, there is no reference that indicates compositions composed of *Aloe barbadensis* metabolites with phospholipids, particularly liposomes that achieve a potent synergy effect.

The present invention provides several concepts applicable to inventiveness, the different components that may be handled in a variety of specific contexts, illustrate the specific ways for use of the compound.

Objective of the present invention is having compositions that incorporate *aloe barbadensis* extract metabolites (aloeride and acemannan) with phospholipids; which may be sphingosomes, ceramides and particularly, liposomes combined with collagen. The *aloe barbadensis* extract in the composition fluctuates in a range comprised between 0.5 and 35% and the liposomes fluctuate in a range comprised between 0.008 at 8%.

These concentrations are found in a relation that achieves an interaction between the *Aloe barbadensis* metabolites and the phospholipids, to obtain the recovery of the epidermis from the diverse lesions already mentioned. The specific concentrations of this new composition are what would lead to the expected results; this being, the synergy activity, a reduction of skin inflammation, and the pimples associated with acne; likewise a reduction in redness of the skin and its structure due to overexposure to UV rays and the external environmental factors that harm the epithelial tissue.

The *Aloe barbadensis* extract in the composition acts as an acne reducing agent in a sufficient amount to reduce redness and inflammation with bacterial exuding associated with acne; in the composition the reducing agent is also used as a cellular conditioner, in quantities that may allow inhibiting or preventing the reappearance of acne. The compositions of the present invention provide a treatment in a way that does not cause skin irritation, with an anti-acne agent in a sufficient amount to reduce redness, also providing photoprotection for the surface of the skin that is exposed to the compound.

The oxidation of the open skin in acne vulgaris, and the pores, determine that the composition has access to the bacteria that cause acne and is able to destroy it. It also acts at a skin grease level oxidizing it, in such a way that it removes the nourishment source for the bacteria that cause acne, additionally avoiding the reappearance of acne. The composition provides a treatment in such a way that it does not irritate the skin, and due to the existing components it acts additionally as a protective factor, being the most important that it does not have side effects such as synthetic substitutes (tretinoine amongst others).

There are other creams in the state of the art, which to avoid the growing of Propionibacterium acnes are added to antibiotics. On the other hand, the present invention does not require the incorporation of antibiotics.

The elimination of Propionibacterium acnes in the present invention is achieved with the variation of the hydrogen potential in the environment of the epithelial surface, which leads to the creation of a hostile environment for bacteria, avoiding the proliferation of the Propionibacterium acnes and in turn avoiding the formation of bacterial detritus. Consequently it is not deposited in the pore thus not creating a cyst in the dermis, typical of complicated acne, and avoids the usual side effects, such as irritation of the skin, cysts and changes in coloration, amongst others. Finally, if in the eventual case a cyst is formed, the present invention decreases the size of the same.

On the other hand, the compound and the compositions of the present invention effectively and efficiently increase the content of phospholipids of the keratinocytes normal in the epidermis. The increasing in lipids has various advantages; it prevents cellular senescence and stimulates their proliferation, increases lipid fractions, amongst them, phospholipids, triglycerides, glucoceramides, ceramides, acilceramides.

Increasing the lipids in the skin, the keratinocytes improve the protective barrier, reduce the atopic dermatitis and protect the skin and body from several harmful agents, amongst them, ultraviolet radiation, toxic chemicals, the increase in phospholipids directly reverts the effects of UV rays, with an improvement in cellular viability and reducing cellular aging.

The compound of the present invention may additionally contain carboxypolymethylene, triethanolamine, propilenglicol, vitamin A and its derivatives, vitamin E, Vitamin C, p-hydroxybenzoates, parabenes and minerals.

The specific concentrations of the components are very important as if they are changed in the composition, the means may not be modified. Especially, the concentration of liposomes is very important as it achieves better transportation of the *Aloe barbadensis*, proving the synergy effect of the new composition.

The compound of the present invention has been developed for topic administration preferring pharmaceutical forms such as lotions, gels, creams, shampoo or another acceptable formulation leading to topic action in the epidermis.

Another objective of the invention is the process of preparation of the compound which consists of the following steps:
a) Obtaining the *aloe* gel from an *aloe* plant that has developed between 2.5 and 6 years (when the concentration of metabolites is found in adequate quantities for the preparation of the compound, greater concentration of aloeride and acemannan).
b) Debridation of the leaf to separate the external cortex and concomitantly separate the product found in the periphery of the internal product found in the central part (the latter being the one used for the process). This process must be carried out in less than 70 minutes to avoid oxidation processes and possible contamination.
c) Add a natural solvent (mineralized water) to the *aloe* gel mixed with carbomers, it is stirred for less than 250 minutes (in this stage of the process a greater stability of the *aloe* gel is obtained).
d) Dissolve the liposomes with natural solvent (mineralized water) plus collagen with propanol 1 diol and add these to the stabilized gel (to ease the transporting capacity).
e) Allow resting for 10 hours to allow the integration of all components.
f) Continually control the pH of the compound maintaining it slightly acidic.

In this process (see literal e) the liposomes plus collagen are added at the end of the process, thus overcoming the problem of the separation of phases. This process is taken to temperatures between 20-50° C. If these ranges are exceeded the functionality of the liposomes will be diminished.

The processes of the state of the art have the following problems:

The *aloe* gel of the sate of the art used for the preparation of creams is extracted from the external part of the *aloe* plant. It has a greater concentration of aloin, for which its application is different with regards to the present invention. It is used as a laxative and may lead to diarrhea, it is not applicable on the skin as it may cause allergic or irritation side effects due to the greater concentration of toxins or irritants.

In the state of the art *aloe* gel from both the external and internal parts of the *aloe* plant is also used with the consequent side effects mentioned in the previous paragraph.

Part of the process for the extraction of the *aloe* gel found in the state of the art consists of suspending the leaf for the gel to drain, requiring a lot of time, which may cause oxidation processes and possible contamination of the products.

All these problems found in the state of the art are overcome by the procedure of the present invention as the extraction is carried out manually in less than 70 minutes, with the intention of reducing the time in which the product is in contact with oxygen in the air, thus avoid oxidation and contamination of the product.

For a better illustration of the invention we present several examples of the making of the same, without this limiting the scope of protection of the present invention.

Example 1

The following example illustrates a preparation of the composition without this being a limitation of components or of the different forms of preparation.

| | |
|---|---|
| *Aloe Barbadensis* Miller Extract | in 0.5 at 35%. |
| Propilenglicol | in 1.1. at 10.5% |
| Coloring | in 0.0010 at 0.0035%. |
| Liposomes | in 0.008 at 8%. |
| Ascorbic acid | in 0.025 at 0.15%. |
| Methyl p-hydroxybenzoate | in 0.009 at 0.5% |
| Natural solvent | in 72 at 92% |

Other excipients to adjust 100% of the compound.

Example 2

10 patients with acne resistant to conventional treatments were observed, who used the invention compound in topical form, and experienced a positive result, with a 95% reduction of lesions; additionally obtaining no relapses of the initial pathology. The aspect of inflammation, pimples and blisters was significantly reduced until disappearing, and no side effect caused by the compound was observed.

REFERENCES

| | | |
|---|---|---|
| U.S. Pat. No. 6,017,554 | January 2000 | Ratcliff |
| U.S. Pat. No. 6,482,839 | November 2002 | Thornfeldt |
| U.S. Pat. No. 6,245,377 | June 2001 | Tao. |
| U.S. Pat. No. 6,713,095 | March 2004 | Maugham et. al. |
| JP patent 62-42733 | July 1987 | |
| U.S. Pat. No. 3,660,566 | May 1972 | Vinson et. al. |
| U.S. Pat. No. 5,565,213 | October 1966 | Nakamori et. al. |

OTHER REFERENCES

Seki et. al. Effect of some alkaloids and flavonoids and triterpenoids, contents of Japanese-Chinese traditional herbal medicine, on the lipogenesis of sebaceous glands. Skin Pharmacol. 681, 56-60 1993.

Griffiths e.al. 1993, Restoration of collagen formation in photo damaged human skin by tretinoin (retinoic acid) New England J. Med 329: 530-5.

Holleran et. al. 1999 Drug treatment of photoaged skin, Drugs & Aging 14: 289-301.

Manez et. al. Effect of selected triterpenoids on chronic dermal inflamation Eur J. Pharmacol, 334: 103-105.

Bombardelli E. Phytosome: New cosmetic delivered system Bolletin Chimico Farmaceutico December 1991 vol 130 No 11 pp 431-438.

Suk Kyo Han et. al. Oleanolic acid and ursolic acid stabilize liposomal membrances, Lipids, II vol 32 No 7, 1997 pp 769-773.

The invention claimed is:

1. A composition for topical administration, consisting essentially of:
    an extract of *Aloe barbadensis* in an amount of from 0.5 to 35 wt % based on the total weight of the composition, the extract consisting essentially of one or more mucilaginous polysaccharides selected from the group consisting of aloeride and acemannan, the one or more mucilaginous polysaccharides present in an amount of 0.001 to 0.15% based on the weight of the extract; and
    one or more liposomes in an amount of 0.008 to 8 wt % based on the total weight of the composition.

2. The composition according to claim 1, wherein the liposomes are in combination with collagen.

3. A composition for topical administration, consisting essentially of:
    an extract of *Aloe barbadensis* in an amount of from 0.5 to 35 wt % based on the total weight of the composition, the extract consisting essentially of one or more mucilaginous polysaccharides selected from the group consisting of aloeride and acemannan, the one or more mucilaginous polysaccharides present in an amount of 0.001 to 0.15% based on the weight of the extract;
    one or more liposomes in an amount of 0.008 to 8 wt % based on the total weight of the composition; and one or more members selected from the group consisting of propylene glycol, ascorbic acid, methyl p-hydroxybenzoate, a parabene, carbopol, triethanolamine, vitamin E, vitamin A, and carboxypolymethylene.

4. The composition according to claim 3, wherein said ascorbic acid is present in an amount of from 0.025 to 0.15 wt % based on the total weight of the composition.

5. The composition according to claim 3, wherein said propylene glycol is present in an amount of from 1.1 to 10.5 wt % based on the total weight of the composition.

6. The composition according to claim 3, wherein said methyl p-hydroxybenzoate is present in an amount of from 0.009 to 0.5 wt % based on the total weight of the composition.

7. The composition of claim 1, in a topical formulation selected from the group consisting of a lotion, a gel, a cream, and a shampoo.

* * * * *